(12) United States Patent
Harrison et al.

(10) Patent No.: US 6,845,267 B2
(45) Date of Patent: Jan. 18, 2005

(54) SYSTEMS AND METHODS FOR MODULATION OF CIRCULATORY PERFUSION BY ELECTRICAL AND/OR DRUG STIMULATION

(75) Inventors: William Vanbrooks Harrison, Valencia, CA (US); Todd K. Whitehurst, Sherman Oaks, CA (US)

(73) Assignee: Advanced Bionics Corporation, Valencia, CA (US)

( * ) Notice: Subject to any disclaimer, the term of this patent is extended or adjusted under 35 U.S.C. 154(b) by 355 days.

(21) Appl. No.: 09/943,550

(22) Filed: Aug. 30, 2001

(65) Prior Publication Data

US 2004/0082978 A1 Apr. 29, 2004

Related U.S. Application Data

(60) Provisional application No. 60/236,420, filed on Sep. 28, 2000.

(51) Int. Cl.[7] .................................................. A61N 1/08

(52) U.S. Cl. ........................................ 607/3; 604/891.1

(58) Field of Search .................... 604/891.1; 128/897, 128/899; 607/1–3, 33, 48, 52, 61, 62, 116

(56) References Cited

U.S. PATENT DOCUMENTS

| 5,193,539 A | 3/1993 | Schulman et al. .......... 128/419 |
| 5,193,540 A | 3/1993 | Schulman et al. .......... 128/419 |
| 5,199,428 A | 4/1993 | Obel et al. ................... 128/419 |

(List continued on next page.)

FOREIGN PATENT DOCUMENTS

| WO | 9837926 | 3/1998 |
| WO | 9843700 | 8/1998 |
| WO | 9843701 | 8/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9 (Sep. 1997), pp. 781–790.

Hammer, L.W., "Differential Inhibition of Functional Dilation of Small Arterioles by Indomethacin and Glibenclamide", Hypertension, vol. 37, No. 2 Part 2 (Feb. 2001), pp. 599–603.

Guimaraes, et al., "Vascular Adrenoceptors: An Update", Pharmacol 53(2) (Rev. Jun. 2001) pp. 319–356.

Hortobagyi, et al., "Randomized Trial of High–Dose Chemotherapy and Blood Cell Autografts for High–Risk Primary Breast Carcinoma", J Natl Cancer Inst 92(3) (Feb. 2, 2000) pp. 225–233.

*Primary Examiner*—Jeffrey P. Jastrzab
*Assistant Examiner*—Frances P. Oropeza
(74) *Attorney, Agent, or Firm*—Laura Haburay Bishop; Bryant R. Gold

(57) ABSTRACT

One or more implantable system control units (SCU) apply one or more stimulating drugs and/or electrical pulses to one or more predetermined areas affecting circulatory perfusion. The SCU preferably includes a programmable memory for storing data and/or control parameters, and preferably uses a power source/storage device, such as a rechargeable battery. If necessary, periodic recharging of such a power source/storage device is accomplished, for example, by inductive coupling with an external appliance. The SCU provides a means of stimulating a nerve(s) or other tissue with electrical and/or infusion pulses when desired, without the need for external appliances during the stimulation session. When necessary, external appliances are used for the transmission of data to and/or from the SCU(s) and/or for the transmission of power. In a preferred embodiment, the system is capable of open- and closed-loop operation. In closed-loop operation, at least one SCU includes a sensor, and the sensed condition is used to adjust electrical and/or drug stimulation parameters.

19 Claims, 8 Drawing Sheets

U.S. PATENT DOCUMENTS

| | | | |
|---|---|---|---|
| 5,324,316 A | 6/1994 | Schulman et al. | 607/61 |
| 5,338,662 A | 8/1994 | Sadri | 435/1 |
| 5,405,367 A | 4/1995 | Schulman et al. | 607/61 |
| 5,494,822 A | 2/1996 | Sadri | 435/284.1 |
| 5,725,563 A | 3/1998 | Klotz | 607/61 |
| 5,916,154 A * | 6/1999 | Hobbs et al. | 600/334 |
| 6,051,017 A | 4/2000 | Loeb et al. | 607/1 |
| 6,058,331 A | 5/2000 | King | 607/62 |
| 6,073,048 A * | 6/2000 | Kieval et al. | 607/17 |
| 6,356,777 B1 * | 3/2002 | Garfield et al. | 600/372 |
| 6,447,443 B1 * | 9/2002 | Keogh et al. | 600/37 |
| 6,464,687 B1 * | 10/2002 | Ishikawa et al. | 604/891.1 |
| 6,571,127 B1 * | 5/2003 | Ben-Haim et al. | 607/40 |

* cited by examiner

SYSTEMS AND METHODS FOR MODULATION OF CIRCULATORY PERFUSION BY ELECTRICAL AND/OR DRUG STIMULATION

The present application claims the benefit of U.S. Provisional Patent Application Ser. No. 60/236,420, filed Sep. 28, 2000, which application is incorporated herein by reference in its entirety.

FIELD OF THE INVENTION

The present invention generally relates to implantable drug delivery and electrical stimulation systems and methods, and more particularly relates to utilizing one or more implantable devices to deliver electrical stimulation and/or one or more stimulating drugs for modulation of circulatory perfusion.

BACKGROUND OF THE INVENTION

Poor circulation is itself a medical condition, and also is often a complication or symptom of other medical conditions. In addition, poor circulation causes additional medical problems, such as ischemia (i.e., localized tissue anemia due to obstruction of the inflow of arterial blood) of various organs and tissue. Ischemia often causes significant pain, and ischemic pain is usually not responsive to narcotics.

In Raynaud's phenomenon, patients suffer painful ischemia, most commonly in the extremities, caused by vasospasm (i.e. acute constriction of arteries and arterioles) in the arterioles supplying the associated region. Also, some headaches likely result from cerebral vasospasm. In another example, patients with cardiac ischemia usually suffer from chest pain, among other symptoms. Severely restricted blood flow in the heart muscle is often caused by atherosclerosis (a disease of the arteries in which fatty material is deposited in the vessel wall, resulting in narrowing and eventual impairment of blood flow).

Arteriosclerosis (a chronic disease characterized by abnormal thickening and hardening of the arterial walls with resulting loss of elasticity) also causes a decrease in circulation. Renal artery stenosis (i.e., narrowing or blockage of the artery that supplies the kidney) is sometimes caused by arteriosclerosis or atherosclerosis. Renal artery stenosis, in turn, often causes hypertension. Another example, peripheral vascular disease, also known as arteriosclerosis of the extremities, occurs in about 6 out of 1,000 people.

These are just a few of the medical conditions that cause or are caused by poor circulation. Existing techniques for increasing blood flow include applying electrical stimulation to the skin, exercise, and vascular bypass grafting.

Other medical conditions cause or are caused by an unusually high rate of blood flow. For instance, some physicians believe that some migraine headaches are due at least in part to vasodilation (i.e., widening of the lumen of blood vessels) of certain cerebral or meningeal (i.e., one of the membranes enveloping the brain and spinal cord) arteries. Existing techniques for decreasing blood flow are primarily based on medication, e.g., sympathomimetic drugs that cause vasoconstriction.

All of the devices currently available for modulating circulatory perfusion have drawbacks. For instance, medications are typically not selective, as they may cause vasoconstriction or vasodilation throughout the body. Vascular bypass grafting is a highly invasive surgical procedure.

A method for treating peripheral vascular disease and organ ischemia by electrical stimulation with closed loop feedback control was published as U.S. Pat. No. 5,199,428 (the '428 patent) and U.S. Pat. No. 6,058,331 (the '331 patent). This method utilizes electrical stimulation of neural tissue. The extent of blood flow in a portion of the patient's body is sensed and neural tissue that project to the portion is electrically stimulated to increase the blood flow. The '331 patent indicates that blood flow is increased by reducing sympathetic neuronal activity in the affected portion of the patient's body. This technique is limited to electrical stimulation, and to applying the electrical stimulation to neural tissue. The '331 patent is further limited to using the electrical stimulation of neural tissue to reduce sympathetic activity.

What is needed is a selection of techniques for modulating circulatory perfusion, which allows physicians and patients to choose the best technique for each unique set of conditions. Also needed is the coupling of circulatory perfusion modulation with the administration of medications, and particularly, a chronic, fully implantable system for modulating circulatory perfusion while administering medication.

BRIEF SUMMARY OF THE INVENTION

As described above, a number of medical conditions and applications benefit from the modulation of circulatory perfusion, i.e., varying the pumping of blood through organs or tissues. Increasing the flow of blood (increasing perfusion) is termed hyperperfusion, while hypoperfusion refers to decreased blood flow through organs or tissue (decreased perfusion).

As detailed below, the invention disclosed and claimed herein provides the modulation of circulatory perfusion, via one or a combination of methods and systems. Some systems and methods of the present invention provide electrical stimulation directly to smooth muscle. Smooth muscle lines all arteries and arterioles, and many organs. Relatively low frequency stimulation tends to excite smooth muscle, leading to contraction. Relatively high frequency stimulation may relax smooth muscle, allowing dilation. Other forms of stimulation (e.g. relatively low frequency currents of 1–10 A applied for 1–30 minutes) will likely lead to relaxation of smooth muscle.

Other systems and methods of the present invention provide the application of a stimulating drug(s) directly to smooth muscle. Neurotransmitters may be infused to affect the smooth muscle by inhibiting autonomic signals, or by simulating autonomic signals.

Additional systems and methods taught herein describe electrical stimulation of autonomic nerves and/or ganglia and/or other sites of autonomic synapses in order to effect modulation of perfusion. Smooth muscle is under autonomic control. The present invention encompasses electrical stimulation of parasympathetic neural tissue, as well as sympathetic tissue stimulation.

In addition, the present invention provides systems and methods for infusing stimulating drugs to modulate circulatory perfusion. As mentioned above, stimulating drugs may be applied directly to smooth muscle of arteries, arterioles, and/or organs. The stimulating drugs may also or instead be applied to autonomic neural tissue. In particular, stimulating drug(s) applied at a neural synapse has an excitatory or inhibitory effect on the signals being transmitted across the synapse.

The present invention also teaches systems and methods for applying electrical and/or drug stimulation to skeletal muscle. The actuation of skeletal muscle provides a pumping action to surrounding blood vessels, and thus plays a role in modulating circulatory perfusion.

Yet other methods and systems taught herein include circulatory perfusion modulation coordinated with the infusion of medication. For instance, applying electrical and/or drug stimulation to cause hypoperfusion in the area targeted for medication helps to keep the medication localized to that area. The medication and stimulation delivery are preferably coordinated. The medication is preferably delivered with the same device as the stimulation, but alternatively, is delivered via another implanted device, or by an external delivery device.

The invention is carried out via one or more system control units (SCU) that apply either electrical stimulation and/or one or more stimulating drugs to one or more predetermined stimulation sites. In one preferred form of an SCU, one or more electrodes are surgically implanted to provide electrical stimulation from an implantable signal/pulse generator (IPG) and/or one or more catheters are surgically implanted to infuse drug(s) from an implantable pump. In another preferred form of an SCU, a miniature implantable neurostimulator, such as a Bionic Neuron (also referred to as a BION® microstimulator), or the like, is implanted.

The SCU preferably includes a programmable memory for storing data, stimulation, and/or control parameters. This allows stimulation and control parameters to be adjusted to levels that are safe and efficacious with minimal discomfort. For instance, the SCU preferably includes a means of stimulating tissue or infusing a stimulating drug(s) either intermittently or continuously. Electrical and drug stimulation may be controlled independently; alternatively, electrical and drug stimulation may be coupled, e.g., electrical stimulation may be programmed to occur only during drug infusion.

According to a preferred embodiment of the invention, the electrodes used for electrical stimulation are arranged as an array on a very thin implantable lead. The SCU is programmed to produce either monopolar electrical stimulation, e.g., using the SCU case as an indifferent electrode, or to produce bipolar electrical stimulation, e.g., using one of the electrodes of the electrode array as an indifferent electrode. The SCU includes a means of stimulating a nerve or infusing a stimulating drug(s) either intermittently or continuously. Specific stimulation parameters may prove more effective for various forms of circulatory perfusion modulation.

The implantable SCU used with the present invention preferably possesses one or more of the following properties:
- at least two electrodes for applying stimulating current to surrounding tissue and/or a pump and at least one outlet for delivering a drug or drugs to surrounding tissue;
- one or more drug infusion outlets;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the SCU; and
- a form factor making the SCU implantable in a target area in the body.

Some embodiments of the stimulator also possess one or both of the following properties:
- leadless; and/or
- a form factor making the SCU implantable via a minimal surgical procedure (e.g., implantable via endoscopy or laparoscopy or injectable via a hypodermic needle).

The power source of the SCU is preferably realized using one or more of the following options:
(1) an external power source coupled to the SCU via a radio-frequency (RF) link;
(2) a self-contained power source made using any means of generation and/or storage of energy, e.g., a primary battery, a replenishable or rechargeable battery, a capacitor, a supercapacitor; and/or
(3) if the self-contained power source is replenishable or rechargeable, means of replenishing or recharging the power source, e.g., an RF link, an optical link, a thermal link, or other energy-coupling link.

According to one embodiment of the invention, an SCU operates independently. According to another embodiment of the invention, an SCU operates in a coordinated manner with other implanted SCUs, other implanted devices, or with devices external to the patient's body.

According to yet another embodiment of the invention, an SCU incorporates means of sensing a circulatory condition or symptoms thereof, or other measures of the state of the patient. Sensed information is preferably used to control the electrical and/or drug stimulation parameters of the SCU in a closed loop manner. According to one embodiment of the invention, the sensing and stimulating means are incorporated into a single SCU. According to another embodiment of the invention, the sensing means communicates sensed information to at least one SOU with stimulating means, i.e., means to supply electric current pulses, and/or infusion means.

Thus, the present invention provides systems and methods for modulating circulatory perfusion that utilize one or more compact, relatively inexpensive SCUs. The implant site is preferably chosen to result in a relatively simple procedure, with the associated advantages in terms of reduced surgical time, expense, possible error, and opportunity for infection. Other advantages of the present invention include the system's monitoring and programming capabilities, the power source, storage, and transfer mechanisms, the activation of the device by the patient or clinician, the system's open and closed loop capabilities, and closed loop capabilities coupled with sensing a need for and/or response to treatment, and coordinated use of one or more SCUs.

BRIEF DESCRIPTION OF THE SEVERAL VIEWS OF THE DRAWINGS

The above and other aspects, features, and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
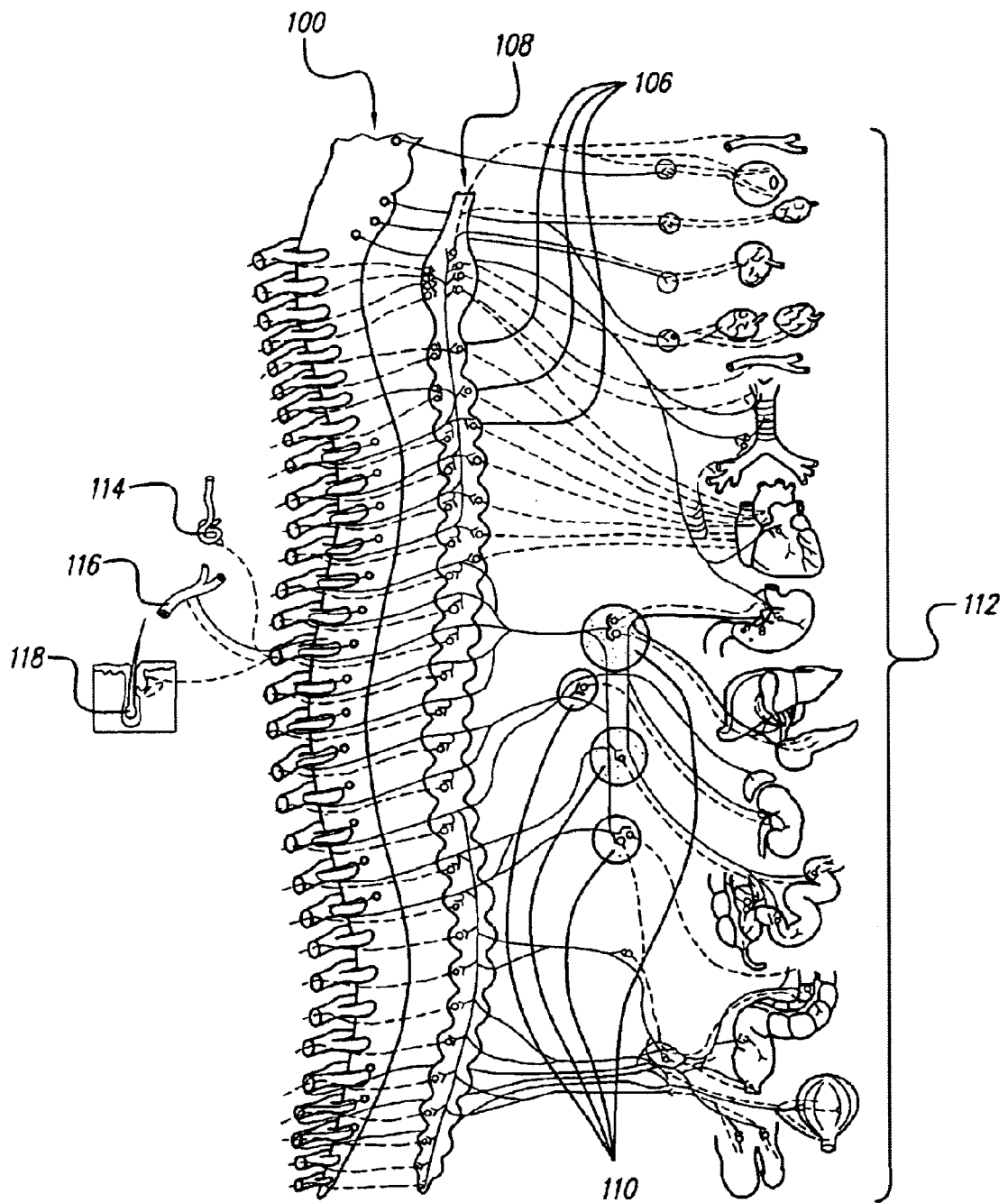
FIG. 1 is a schematic of the autonomic nervous system.
Figure 2:
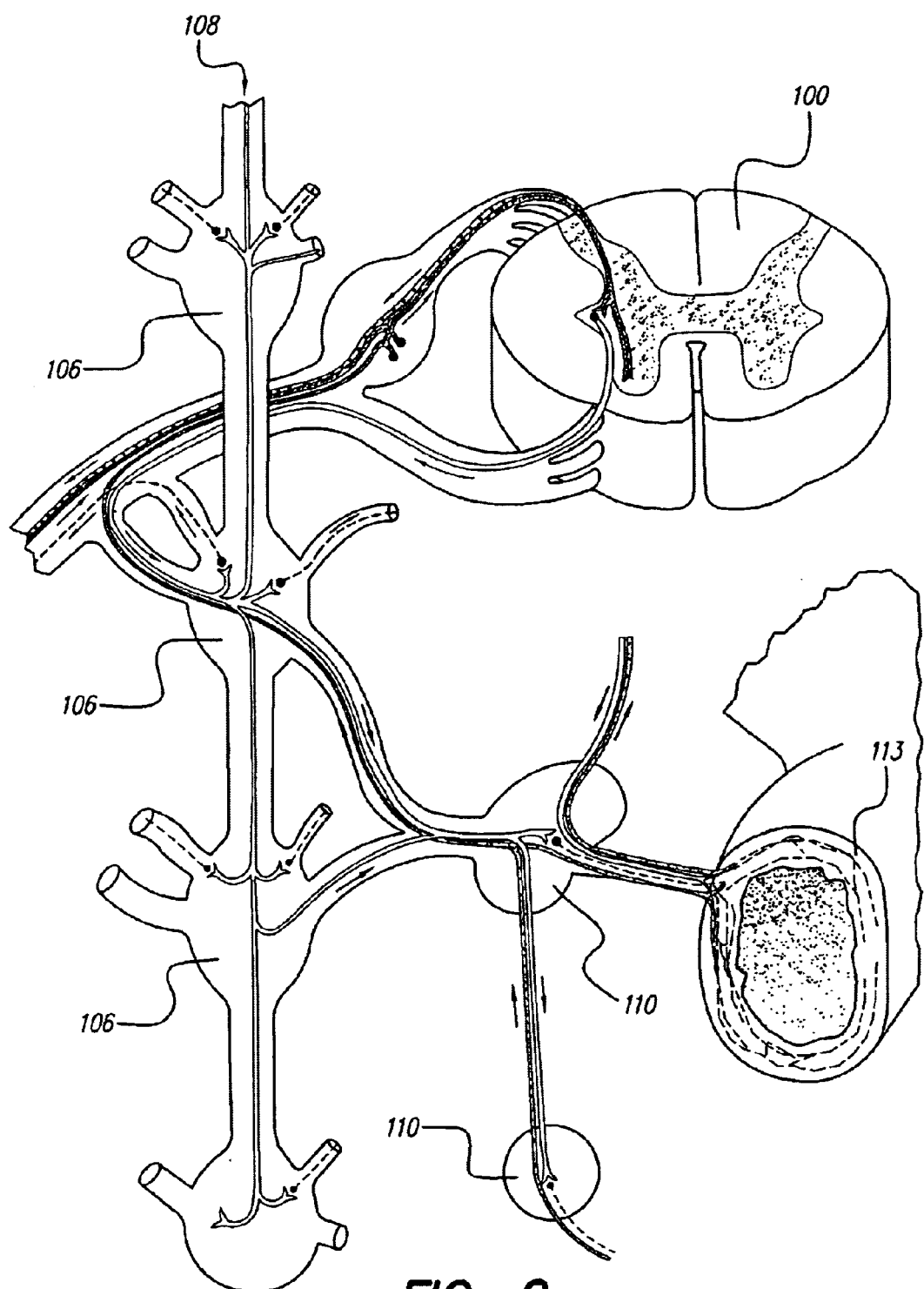
FIG. 2 depicts the nerve pathways in and near the thoracic part of the spinal cord.

FIG. 1 is a schematic of the autonomic nervous system and FIG. 2 illustrates nerve pathways in and near the thoracic portion of the spinal cord. Sympathetic fibers originate in the spinal cord 100 then travel a short distance to ganglia 106 of the sympathetic trunk 108. Most sympathetic fibers synapse in the sympathetic trunk ganglia 106, while other sympathetic fibers travel through the sympathetic trunk ganglia 106 and synapse at ganglia 110 distributed throughout the body. The postsynaptic sympathetic fibers travel from the various ganglia 106 and 110 to the respective muscles, organs and glands 112 to be innervated. In the sympathetic innervation example of FIG. 2, the organ 112 being innervated is a section of the intestines 113. Additional glands and muscles are innervated by postsynaptic sympathetic fibers at each level of the spinal cord. These include sweat glands 114, smooth muscle surrounding blood vessels 116, and the arrector (i.e. smooth) muscle of the hair follicle 118.

Figure 3:
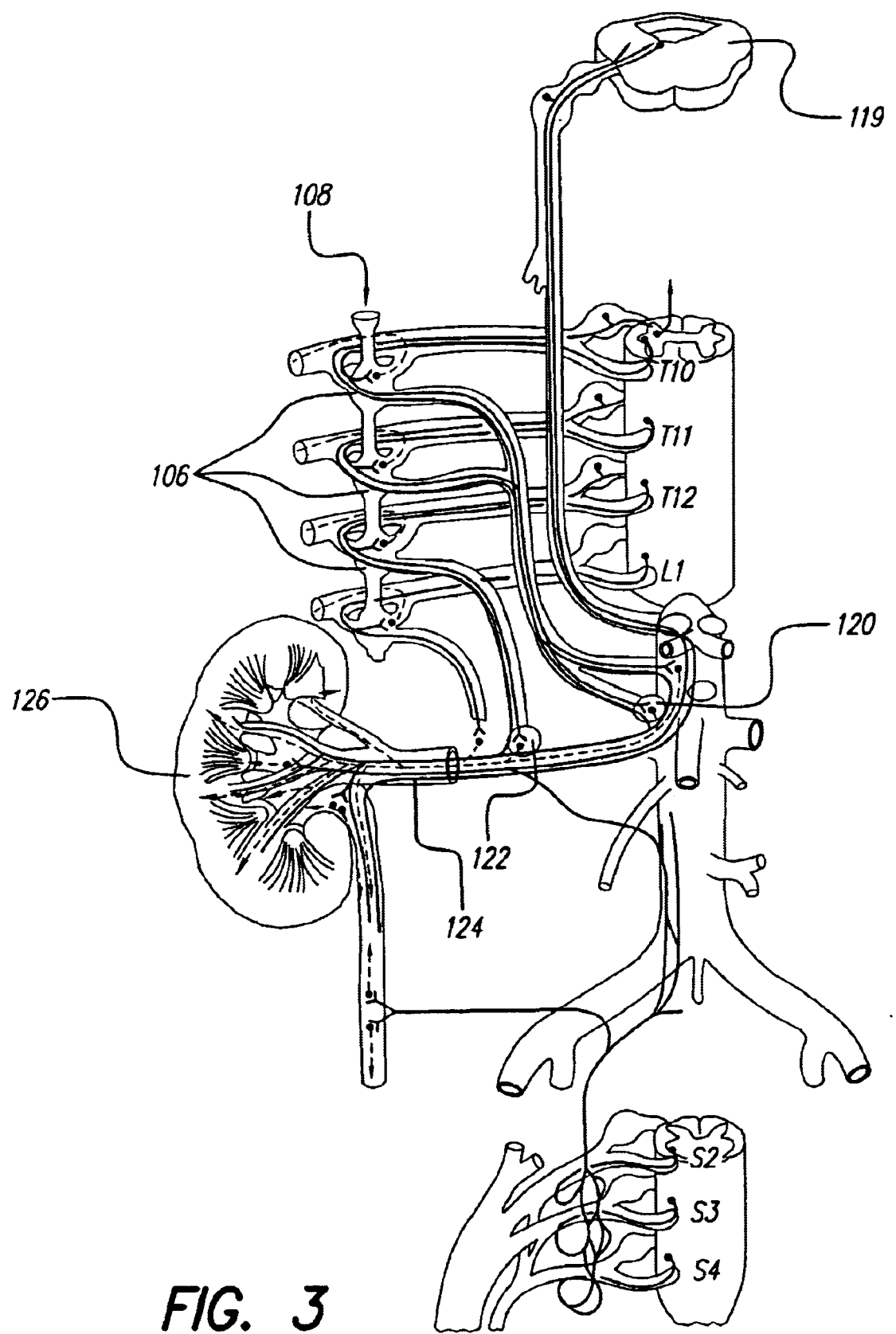
FIG. 3 depicts the innervation of the kidneys and upper ureters.

As a further example, FIG. 3 depicts the innervation of a kidney. Sympathetic signals traveling to the kidney originate mainly from spinal segments T10–T12 and L1. Parasympathetic signals originate mainly from spinal segments S2–S4 and from the medulla oblongata 119. The sympathetic signals travel through the sympathetic trunk ganglia 106, where some may synapse, while others synapse at the aorticorenal ganglion 120 and the renal ganglion 122. The postsynaptic sympathetic signals then travel along the renal artery 124 to the kidney 126. Presynaptic parasympathetic signals travel to sites near the kidney before they synapse on or near the organ.

Most arteries and arterioles are lined with smooth muscle that controls vessel diameter. Additionally, some organs, such as the gastrointestinal (GI) tract and the lungs, contain smooth muscle that modulates organ function. This smooth muscle is under autonomic control. Increased sympathetic activity tends to contract the smooth muscle, which, for instance, shrinks the diameter of arteries or arterioles. Decreased sympathetic activity tends to have the opposite effect, and allows the smooth muscle to relax, so for instance, the vessels dilate. Conversely, increased parasympathetic activity tends to relax smooth muscle, while decreased parasympathetic activity tends to contract smooth muscle.

Electrical stimulation may be applied to affect the activity of autonomic nerve fibers. For example, relatively low frequency neurostimulation (i.e., less than about 50–100 Hz) generally has an excitatory effect on neural tissue, whereas relatively high frequency neurostimulation (i.e., greater than about 50–100 Hz) may have an inhibitory effect. Thus, electrical stimulation may be applied to sympathetic and/or parasympathetic nerves, ganglia, and/or other sites of autonomic synapses in order to effect modulation of circulatory perfusion, as discussed in more detail presently.

Stimulating drugs may also be used to simulate activity of the autonomic nervous system. For instance, sympathetic excitatory neurotransmitter agonists (i.e., sympathetic agonists), such as adrenergic receptor agonists (e.g., norepinephrine), generally have an excitatory effect on sympathetic targets, while sympathetic excitatory neurotransmitter antagonists (i.e., sympathetic antagonists), such as adrenergic receptor antagonists (e.g., phentolamine) generally have an inhibitory effect on sympathetic targets. Similarly, parasympathetic excitatory neurotransmitter agonists (i.e., parasympathetic agonists), such as cholinergic receptor agonists (e.g., bethanechol), generally have an excitatory effect on parasympathetic targets, while parasympathetic excitatory neurotransmitter antagonists (i.e., parasympathetic antagonists), such as cholinergic receptor antagonists (e.g., atropine), generally have an inhibitory effect on parasympathetic targets. In addition, inhibitory neurotransmitter antagonists, such as gamma-aminobutyric acid (GABA) antagonists (e.g., bicuculline), also have an excitatory effect, while inhibitory neurotransmitter agonists, such as GABA agonists (e.g., diazepam), generally have an inhibitory effect.

Herein, stimulating drugs comprise medications, anesthetic agents, synthetic or natural hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug.

Electrical stimulation may be applied directly to smooth muscle to modulate its contractile state. Relatively low frequency electrical stimulation than about 50–100 Hz) tends to excite smooth muscle and lead to contraction. Other forms of stimulation, e.g., relatively low frequency currents (e.g., of 1–10 mA applied for 1–30 minutes), lead to relaxation of smooth muscle through arterialization, in which the applied current causes vasodilation. Relatively high frequency electrical stimulation tends to relax smooth muscle and lead to dilation. Electrical stimulation may thus be used to modulate the circulatory perfusion of tissue.

Drug stimulation may also be used to modulate perfusion of tissue. For instance, infusing a sympathetic excitatory neurotransmitter antagonist or a sympathetic inhibitory neurotransmitter agonist into sympathetic ganglia or other sites of sympathetic synapses reduces sympathetic stimulation of the innervated tissues. As mentioned above, the decreased sympathetic activity allows the smooth muscle to relax, which in turn allows increased perfusion. Conversely, infusing a sympathetic excitatory neurotransmitter agonist or a sympathetic inhibitory neurotransmitter antagonist into sympathetic ganglia or other sites of sympathetic synapses increases sympathetic innervation, which leads to contraction of the smooth muscle and decreased perfusion. Similarly, stimulating drugs may be infused at parasympathetic synapses to modulate the parasympathetic signal.

In addition to applying stimulating drugs at one or more autonomic ganglia or other sites of autonomic synapses, the drug(s) are alternatively or additionally applied to the tissue that is ultimately affected by the autonomic signals. As an example, a drug(s) may be delivered via the bloodstream by applying the drug(s) to vascular tissue (e.g., infused into one or more arteries or veins). Alternatively or additionally, the drug(s) may be delivered directly to other targeted tissue. This causes the smooth muscle to interpret a sympathetic excitatory neurotransmitter agonist as a sympathetic signal, for example. An inhibitory neurotransmitter may be used to allow increased effect of natural autonomic signals, for example, or other applied stimulation.

Other drugs also affect modulatory perfusion. Indomethacin attenuates arteriolar vasodilation in larger arterioles. Glibenclamid attenuates arteriolar vasodilation in both larger and smaller arterioles. Nitric oxide and related medications such as nitroglycerin promote vasodilation. Several different types of prostaglandins also promote vasodilation, e.g., Prostaglandin $E_2$ ($PGE_2$) and Prostaglandin $F_{2\alpha}$.

In addition to smooth muscle, skeletal muscle plays a role in the modulation of circulatory perfusion. (Cardiac muscle also plays a role, but the present invention is not directed to stimulation of cardiac tissue.) As skeletal muscle is actuated, it contracts and expands, which pushes on surrounding tissue. This creates a pumping action for the blood in surrounding vessels. For instance, when walking, the muscles of the leg aid in blood circulation by alternately pushing on the blood vessels, then relaxing. This pumping action may be simulated by properly stimulating the skeletal muscle to make it contract, and either stimulating it to relax or allowing time for the muscle to relax between stimulation cycles. Stimulating skeletal muscle with relatively high-frequency electrical stimulation tends to cause skeletal muscle to relax, while relatively low frequency electrical stimulation causes the skeletal muscle to contract. Modulating the electrical stimulation frequency therefore advantageously modulates the contractile state of the muscle, which in turn modulates circulatory perfusion.

Thus, as discussed in more detail presently, the methods and systems of the present invention are useful to modulate circulatory perfusion. There are numerous medical applications for circulatory perfusion modulation. Some of these medical applications are presented herein, while others applications will be apparent to those of skill in the art upon review of the present description.

Hypoperfusion (i.e., less than normal amount of fluid supplied to an organ or tissues) may be applied therapeutically to restrict medication to a local area. For example, local anesthetics are often administered along with a sympathetic agonist (e.g., epinephrine) to restrict perfusion. This prolongs the activity of the anesthetic in the local tissue. Local hypoperfusion is likely to be most useful in its application to chemotherapy. Tumors are usually localized to a certain area, but chemotherapy agents are typically administered intravenously and thus produce effects systemically. However, chemotherapy applied to a local area, e.g., through a percutaneous line or catheter, coupled with hypoperfusion of the local area would advantageously result in prolonged activity of the chemotherapy agent in the tumor site and thus perhaps decrease systemic effects.

Induction of hypoperfusion is also likely to have an application for migraine headaches. Some physicians believe that migraine headaches are due at least in part to vasodilation of certain cerebral or meningeal (i.e., one of the membranes enveloping the brain and spinal cord) arteries. Constriction of these vessels might prove therapeutic.

Hyperperfusion (i.e., more than normal amount of fluid supplied to an organ or tissue) may be applied therapeutically for other medical applications. By increasing the perfusion in areas targeted for medication, systemically administered medications are likely focused into the target areas. For example, systemically administered chemotherapy agents may be focused to a tumor site(s) and systemically administered antibiotics may be focused on an infection site(s), such as an abscess. In addition, hyperperfusion may be used to preferentially deliver medications that affect specific tissues or organs, e.g., diuretics to the kidney or anti-inflammatory agents to arthritic joints.

In addition, some medical conditions result in constriction of arteries and arterioles, which is likely to cause ischemia of the related organs and tissues. Acute constriction is referred to as vasospasm. Ischemic tissue will benefit from increased perfusion, and the resulting boost in oxygen delivery. For example, dilation of coronary arteries will likely provide beneficial during cardiac ischemia. In Raynaud's phenomenon, patients suffer painful ischemia, most commonly in the extremities, caused by vasospasm in the arterioles supplying the associated region. Induction of hyperperfusion will thus result in symptomatic relief. Also, some headaches result from cerebral vasospasm; arterial dilation will therefore produce relief.

Hypertension may be relieved with the administration of selective alpha-adrenoceptor sympathetic antagonists (e.g., phentolamine); these redilation, which is at least partly responsible for the subsequent decrease in blood pressure. Alpha-adrenoceptors may be categorized into subtypes. Specifically, alpha(1)-adrenoceptors (primarily) and alpha (2B)-adrenoceptors (secondarily) contribute to the peripheral regulation of vascular tone.

As indicated above, arterial dilation may also or instead be instigated by electrical stimulation applied directly to the smooth muscle or to the autonomic nerves innervating these arteries. Selective dilation of pulmonary arteries and arterioles may, for some patients, prove therapeutic for pulmonary hypertension.

Thus, to modulate circulatory perfusion in accordance with the teachings of the present invention, stimulation is provided via electrical stimulation and/or one or more stimulating drugs. In some preferred alternatives, one or more system control units (SCUs) comprising an implantable signal generator and electrode(s) and/or an implantable pump and catheter(s) are used to deliver electrical stimulation and/or one or more stimulating drugs to specific targeted areas. One or more electrodes are surgically implanted to provide electrical stimulation, and/or one or more catheters are surgically implanted to infuse the stimulating drug(s).

Figure 4A:
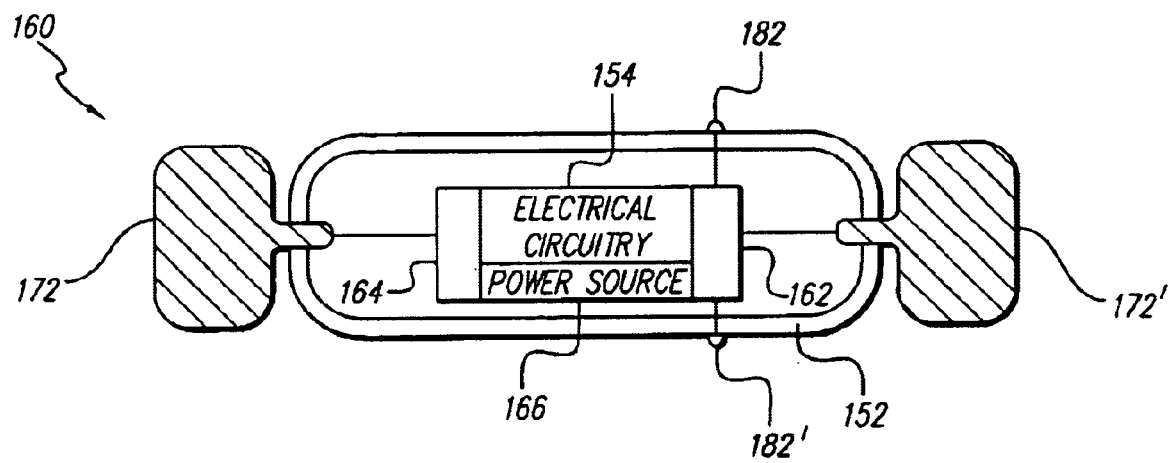
FIGS. 4A, 4B, and 4C show possible configurations of an implantable microstimulator of the present invention.
Figure 4B:
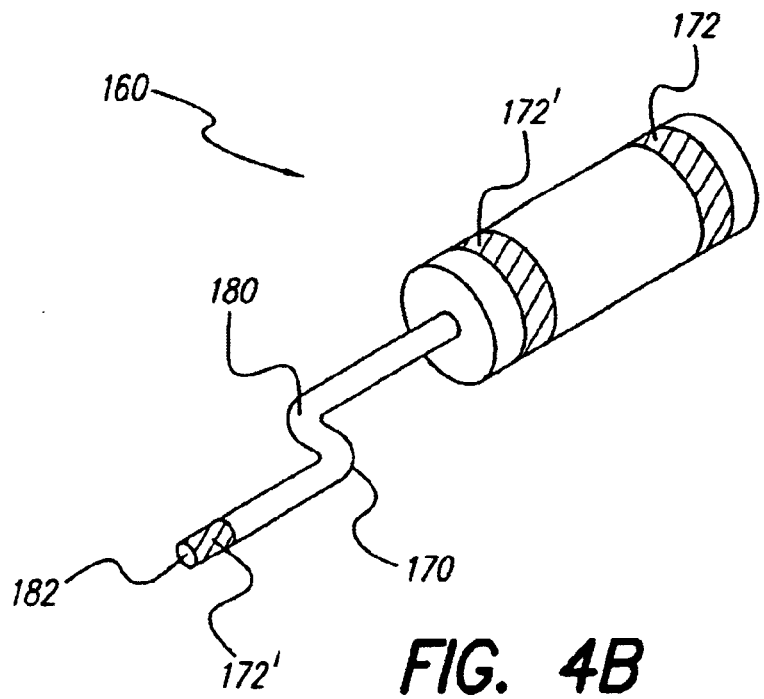
Figure 4C:
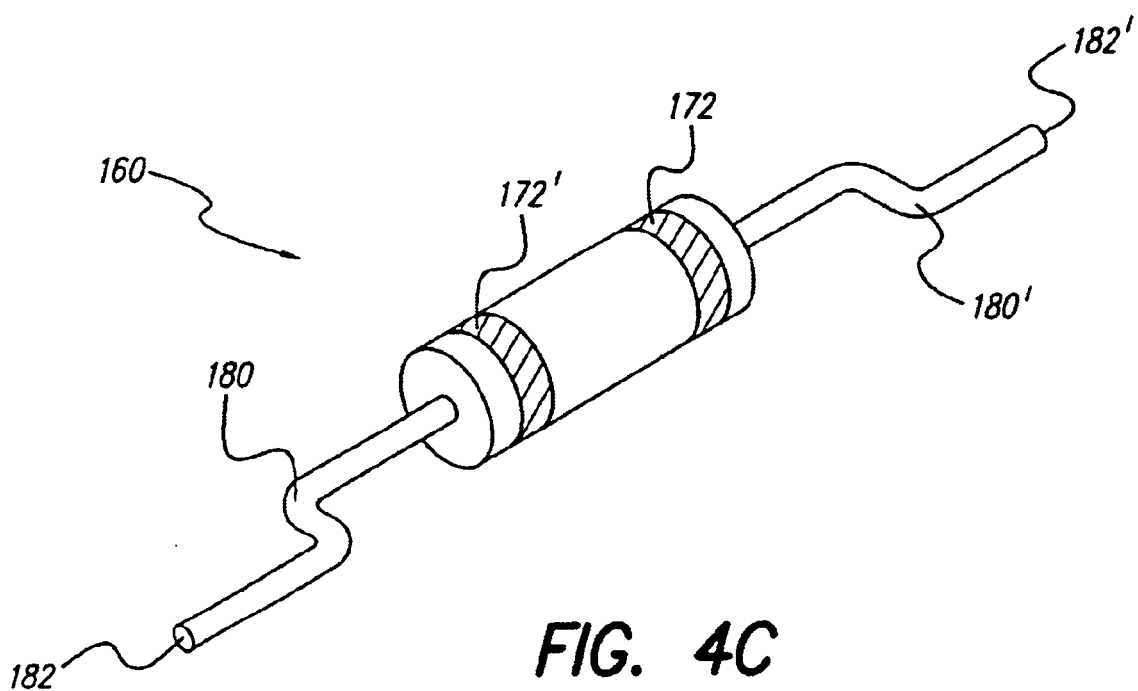

In other preferred embodiments, stimulation is provided by one or more SCUs that are small, implantable neurostimulator(s), referred to herein as microstimulators. The microstimulator SCUs of the present invention are preferably (but not necessarily) the type referred to as BION® devices, or similar (FIGS. 4A, 4B, 4C). The following documents describe various features and details associated with the manufacture, operation and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |

-continued

| Application/Patent/<br>Publication No. | Filing/Publication<br>Date | Title |
|---|---|---|
| U.S. Pat. No. 5,312,439 | Issued<br>May 17, 1994 | Implantable Device Having<br>an Electrolytic Storage<br>Electrode |
| U.S. Pat. No. 5,324,316 | Issued<br>Jun. 28, 1994 | Implantable<br>Microstimulator |
| U.S. Pat. No. 5,405,367 | Issued<br>Apr. 11, 1995 | Structure and Method of<br>Manufacture of an<br>Implantable<br>Microstimulator |
| PCT Publication<br>WO 98/37926 | Published<br>Sep. 3, 1998 | Battery-Powered Patient<br>Implantable Device |
| PCT Publication<br>WO 98/43700 | Published<br>Oct. 8, 1998 | System of Implantable<br>Devices For Monitoring<br>and/or Affecting Body<br>Parameters |
| PCT Publication<br>WO 98/43701 | Published<br>Oct. 8, 1998 | System of Implantable<br>Devices For Monitoring<br>and/or Affecting Body<br>Parameters |
| U.S. Pat. No. 6,051,017<br>(App. 09/077,662) | Issued<br>Apr. 18, 2000 | Improved Implantable<br>Microstimulator and<br>Systems Employing<br>Same |
|  | Published<br>September, 1997 | Micromodular Implants to<br>Provide Electrical<br>Stimulation of Paralyzed<br>Muscles and Limbs, by<br>Cameron, et al., published<br>in IEEE Transactions<br>on Biomedical Engineering,<br>Vol. 44, No. 9,<br>pages 781–790. |

As seen in FIGS. 4A, 4B, and 4C, preferred microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 4B) or at the end of a lead, as described below. As detailed in the referenced patents, electrodes 172 and 172' preferably comprise a stimulating electrode (to be placed close to the target tissue) and an indifferent electrode (for completing the circuit). Other preferred configurations of microstimulator SCU 160 are possible, as is evident from the above-referenced patent publications, and as described in more detail herein.

Advantageously, implantable microstimulator SCU 160 is sufficiently small to permit its placement in or near the structures to be stimulated. Capsule 152 preferably has a diameter no greater than about 4–5 mm, more preferably only about 3 mm, and most preferably less than 3 mm. Capsule length is preferably no greater than about 25–35 mm, more preferably only about 20–25 mm, and most preferably less than 20 mm. The shape of the microstimulator is preferably determined by the structure of the desired target, the surrounding area, and the method of implantation. A thin, elongated cylinder with electrodes at the ends, as shown in FIGS. 4A, 4B, and 4C, is one preferred configuration, but other shapes, such as rounded cylinders, disks, spheres, and helical structures, are possible, as are additional electrodes, infusion outlets, leads, and/or catheters.

In addition, the length and/or shape of an SCU 160 may be varied in order to monitor more effectively and/or deliver more effective treatment. For example, if the SCU is a thin cylindrical device with an electrode at each end, the length of this device may be varied to apply stimulation to tissues of different sizes. As another example, if the SCU is a flat circular (i.e., pancake-shaped) stimulator device with electrodes distributed around its periphery, the diameter of this device may be varied to treat tissues of different sizes. As yet another example, the size of a substantially spherical device may be varied to treat different sizes of tissues.

Microstimulator SCU 160, when used, is preferably implanted with a surgical insertion tool specially designed for the purpose, or is injected (e.g., via a hypodermic needle). Alternatively, microstimulator SCU 160 may be implanted via conventional surgical methods, or may be inserted using other endoscopic or laparoscopic techniques. A more complicated surgical procedure may be required for fixing the microstimulator in place.

The external surfaces of microstimulator SCU 160 are advantageously composed of biocompatible materials. Capsule 152 is preferably made of glass, ceramic, or other material that provides a hermetic package that will exclude water vapor but permit passage of electromagnetic fields used to transmit data and/or power. Electrodes 172 and 172' are preferably made of a noble or refractory metal or compound, such as platinum, iridium, tantalum, titanium, titanium nitride, niobium, or alloys of any of these, in order to avoid corrosion or electrolysis which could damage the surrounding tissues and/or the device.

In one preferred embodiment of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads may permit electrical stimulation to be directed more locally to a specific nerve, nerve branch, or other targeted tissue (such as smooth or skeletal muscle) a short distance from the surgical fixation of the bulk of the implantable microstimulator SCU 160, while allowing most elements of the microstimulator to be located in a more surgically convenient site. This minimizes the distance traversed and the surgical planes crossed by the device and any lead(s). In a preferred embodiment, the leads are no longer than about 150 mm.

As mentioned earlier, the invention includes at least one SCU. In the case of electrical stimulation only, preferred SCUs include a microstimulator and/or an implantable pulse/signal generator (IPG). In the case of drug infusion only, a preferred SCU comprises an implantable pump. In cases requiring both electrical stimulation and drug infusion, one or more SCUs are used. Alternatively and preferably, when needed, an SCU provides both electrical stimulation and one or more stimulating drugs.

Figure 5:
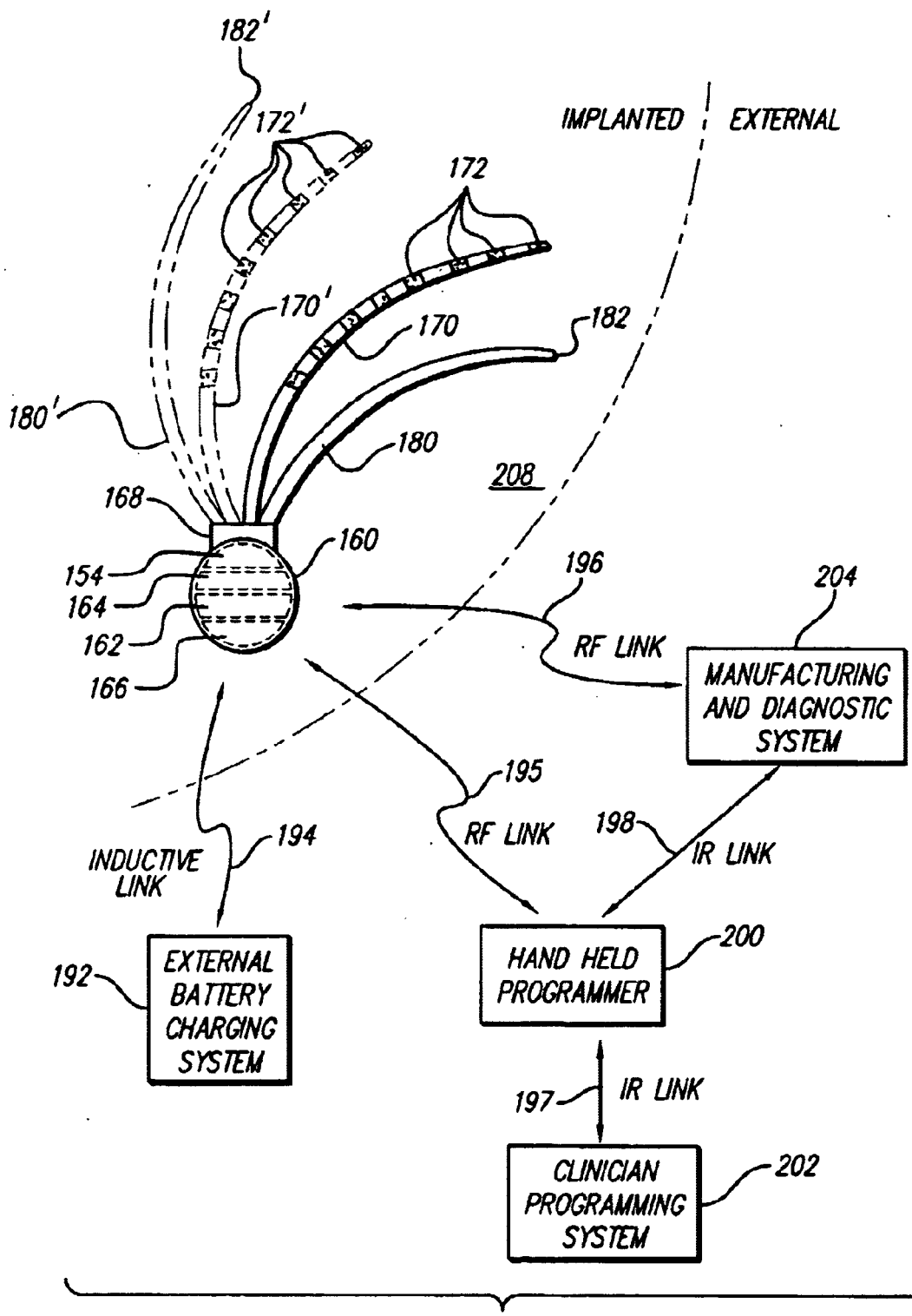
FIG. 5 illustrates internal and external components of an exemplary embodiment of the invention.

As depicted in the preferred embodiment of FIG. 5, SCU 160 is preferably (but not necessarily) implanted in a surgically-created shallow depression or opening in the abdomen or above the buttock. SCU 160 may be implanted in other locations, such as in a limb. SCU 160 preferably conforms to the profile of surrounding tissue(s) and/or bone(s), and is small and compact. This is preferable so that no unnecessary pressure is applied to the skin, as this may result in skin erosion or infection. SCU 160 preferably has a diameter of no greater than 75 mm, more preferably no greater than 65 mm, and most preferably about 35–55 mm. SCU thickness of approximately 10–12 mm is preferred, while a thickness of about 8–10 mm or less is more preferred.

As seen in FIG. 5, one or more electrode leads 170 and/or catheters 180 attached to SCU 160 run in a surgically-created shallow groove(s) or channel(s) subcutaneously or in a fascial plane(s). Recessed placement of the SCU and the lead(s) and/or catheter(s) has the advantages of decreased likelihood of erosion of the overlying skin, and of minimal cosmetic impact.

In this preferred case of treatment with electrical stimulation, electrode(s) 172 are carried on lead 170 having a proximal end coupled to SCU 160. The lead contains wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, the case of the SCU is preferably hermetically sealed. For additional protection against, e.g. impact, the case is preferably made of metal (e.g. titanium) or ceramic, which materials are also, advantageously, biocompatible. In addition, SCU 160 is preferably Magnetic Resonance Imaging (MRI) compatible.

In the case of treatment alternatively or additionally constituting drug infusion SCU 160 preferably contains at least one pump 162 for storing and dispensing one or more drugs through outlet(s) 182 and/or catheter(s) 180 into a predetermined site. When a catheter is used, it preferably includes at least one outlet(s) 182, usually positioned at least at a distal end, while a proximal end of the catheter is connected to SCU 160.

SCU 160 (which herein refers to IPGs, implantable pumps, IPG/pump combinations, microstimulators for drug and/or electrical stimulation, and/or other alternative devices described herein) preferably contains electronic circuitry 154 for receiving data and/or power from outside the body by inductive, radio frequency (RF), or other electromagnetic coupling. In a preferred embodiment, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also advantageously includes a programmable memory 164 for storing a set(s) of data, stimulation, and control parameters. This feature allows electrical and/or drug stimulation to be adjusted to settings that are safe and efficacious with minimal discomfort for each individual. Specific parameters may provide therapeutic advantages for various conditions that benefit from modulation of circulatory perfusion. For instance, some patients may respond favorably to intermittent stimulation, while others may require continuous treatment for relief. Electrical and drug stimulation parameters are preferably controlled independently, e.g., in the preferred embodiment of continuous electrical stimulation and no drug stimulation. However, in some instances, they are advantageously coupled, e.g., electrical stimulation may be programmed to occur only during drug infusion.

In addition, parameters may be chosen to target specific neural populations and to exclude others, or to increase neural activity in specific neural populations and to decrease neural activity in others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) typically has an inhibitory effect, leading to decreased neural activity. Furthermore, neurotransmitters may be administered to target the inhibition or excitement of sympathetic or parasympathetic tissue, as described earlier.

The preferred SCU 160 also includes a power source and/or power storage device 166. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link, an optical link, a thermal link, or other energy-coupling link).

In one preferred embodiment shown in FIG. 5, SCU 160 includes a rechargeable battery as a power source/storage device 166. The battery is recharged, as required, from an external battery charging system (EBCS) 192, typically through an inductive link 194. In this embodiment, SCU 160 includes a processor and other electrical circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and rates of infusion, such as intermittent infusion, infusion at a constant rate, and bolus infusion.

According to preferred embodiments of the invention, such as depicted in FIG. 5, at least one lead 170 is attached to SCU 160, via a suitable connector 168, if necessary. Each lead includes at least two electrodes 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, SCUs 160 of FIGS. 4A, 4B, and 4C have outlets 182, 182' for infusing a stimulating drug(s) and electrodes 172, 172' for applying electrical stimulation.

Lead(s) 170 are preferably less than 5 mm in diameter, and more preferably less than 1.5 mm in diameter. Electrodes 172, 172' on leads are preferably arranged as an array, more preferably are at least two collinear electrodes, and most preferably at least 4 collinear electrodes. A tip electrode may also be supplied at the distal end of one or more leads. SCU 160 is preferably programmable to produce either monopolar electrical stimulation, e.g., using the SCU case as an indifferent electrode, or bipolar electrical stimulation, e.g., using one of the electrodes of the electrode array as an indifferent electrode. A preferred SCU 160 has at least four channels and drives up to sixteen electrodes or more.

According to one embodiment of the invention, an SCU operates independently. According to another embodiment of the invention, an SCU operates in a coordinated manner with other SCU(s), other implanted device(s), or other device(s) external to the patient's body. For instance, an SCU may control or operate under the control of another implanted SCU(s), other implanted device(s), or another device(s) external to the patient's body. An SCU may communicate with other implanted SCU(s), other implanted device(s), and/or device(s) external to a patient's body via, e.g., via an RF link, an ultrasonic link, or an optical link. Specifically, an SCU may communicate with an external remote control (e.g., patient and/or physician programmer) that is capable of sending commands and/or data to an SCU and that is preferably capable of receiving commands and/or data from an SCU.

For example, according to the embodiment of FIG. 5, SCU 160 may be activated and deactivated, programmed and tested through a hand held programmer (HHP) 200 (which may also be referred to as a patient programmer and is preferably, but not necessarily, hand held), a clinician programming system (CPS) 202 (which may also be hand held), or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through RF link 196, or indirectly through IR link 198, HHP 200, and RF link 195.

Figure 6:
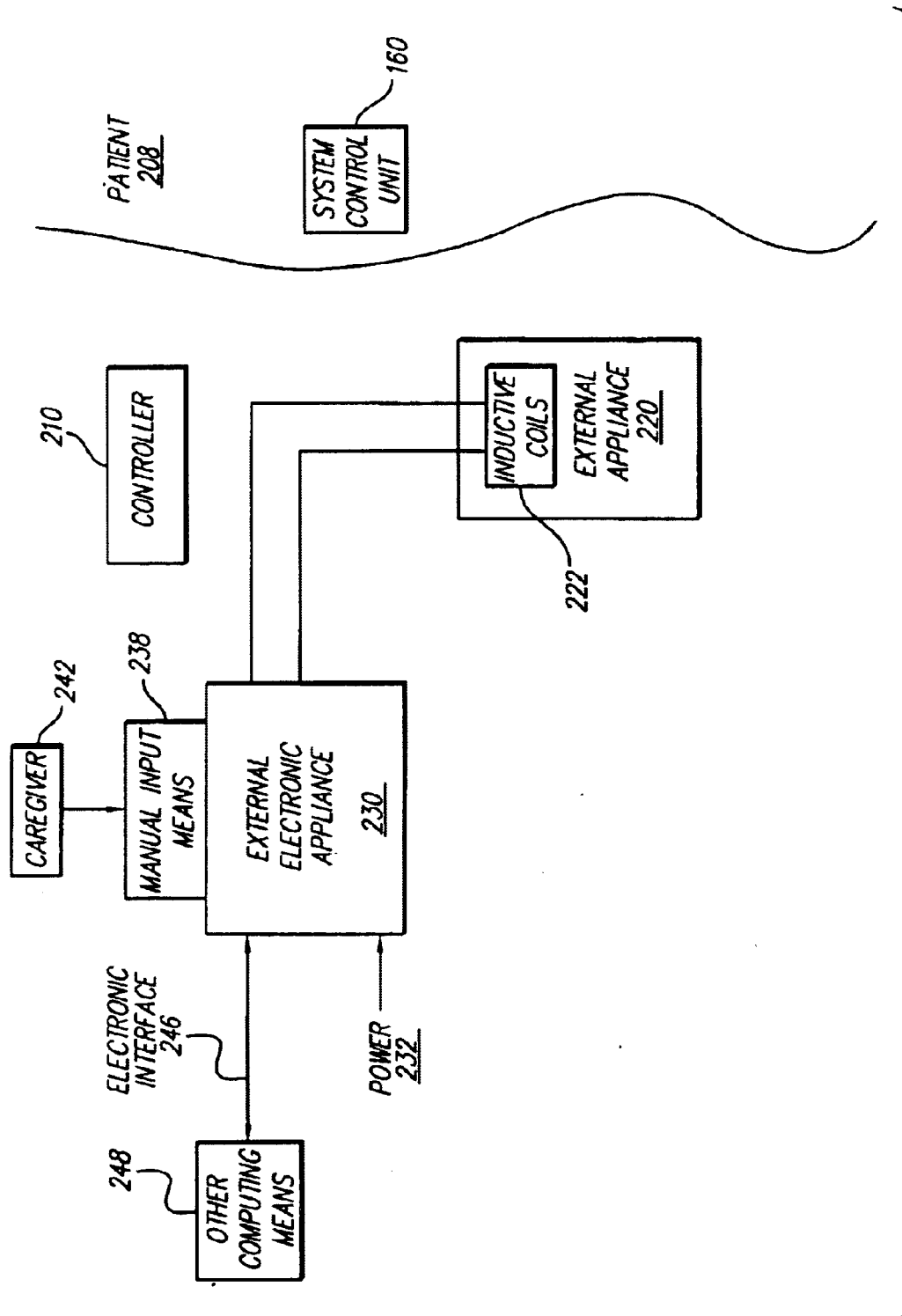
FIG. 6 illustrates internal and external components of an additional exemplary embodiment of the invention.

In another preferred embodiment, using for example, a BION microstimulator(s) as described in the above referenced patents, and as illustrated in FIG. 6, the patient 208 switches SCU 160 on and off by use of controller 210, which is preferably handheld. Controller 210 operates to control SCU 160 by any of various means, including sensing the proximity of a permanent magnet located in controller 210, or sensing RF transmissions from controller 210.

External components of one preferred embodiment for programming and providing power to SCU 160 are also illustrated in FIG. 6. When it is required to communicate with SCU 160, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which receives power 232 from a conventional power source. External appliance 230 contains manual input means 238, e.g., a keypad, whereby the patient 208 or a caregiver 242 may request changes in electrical and/or drug stimulation parameters and/or control parameters used during the normal operation of SCU 160. In this preferred embodiment, manual input means 238 includes various electro-mechanical switches and visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem. Such interface means 246 thus permits a clinician to monitor the status of the implant and prescribe new stimulation parameters from a remote location.

The external appliance(s) may advantageously be embedded in a cushion, pillow, mattress cover, or garment. Other possibilities exist, including a belt or other structure that may be affixed to the patient's body or clothing.

In order to help determine the strength and/or duration of electrical stimulation and/or the amount and/or type(s) of stimulating drug(s) required to produce the desired effect, in one preferred embodiment, a patient's response to and/or need for treatment is sensed. For example, pressure (e.g. arterial blood pressure), blood flow (e.g., by direct flow sensor or by indirect means such as Doppler ultrasound), arterial oxygen saturation (via pulse oximetry), acidity/alkalinity (via a pH sensor), muscle activity (e.g., EMG), nerve activity (e.g., ENG), electrical activity of the brain (e.g., EEG), impedance, or other activity is recorded to determine need for or in response to electrical and/or drug stimulation from SCU 160.

For example, when electrodes of SCU 160 are implanted near renal artery 124, a stimulating electrode (or a separate electrode) of SCU 160 preferably senses changes in blood pressure resulting from the stimulation applied to the smooth muscle surrounding renal artery 124. (As used herein, "near" means as close as reasonably possible to targeted tissue, including touching or even being positioned within the tissue, but in general, may be as far as about 150 mm from the target tissue.) Alternatively, an "SCU" dedicated to sensory processes communicates with an SCU that provides the electrical and/or infusion pulses. The implant circuitry 154 may, if necessary, amplify and transmit these sensed signals, which may be digital or analog. Other methods of determining the required electrical and/or drug stimulation include measuring neurotransmitter levels and/or their associated breakdown product levels, measuring medication and/or other drug levels, hormone levels, and/or levels of any other bloodborne substance(s), such as cytokines or enzymes, and/or changes in one or more of these, other methods mentioned herein, and others that will be evident to those of skill in the art upon review of the present disclosure. The sensed information is preferably used to control stimulation parameters in a closed-loop manner.

For instance, in one embodiment of the present invention, a first and second "SCU" are provided. The second "SCU" periodically (e.g. once per minute) records arterial blood pressure, which it transmits to the first SCU. The first SCU uses the sensed information to adjust electrical and/or drug stimulation parameters according to an algorithm programmed, e.g., by a physician. For example, the amplitude of electrical stimulation may be increased in response to decreased pressure. More preferably, one SCU performs both the sensing and stimulating functions, as discussed in more detail presently.

While an SCU 160 may also incorporate means of sensing improper circulatory perfusion, e.g., via arterial pressure or electromyograph, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback.

Thus, it is seen that in accordance with the present invention, one or more external appliances are preferably provided to interact with SCU 160 to accomplish one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation produced by SCU 160.

Function 3: Transmit sensed data indicating a need for treatment or in response to stimulation from SCU 160 (e.g., blood pressure, blood flow, arterial oxygen saturation, muscle activity, nerve activity, electrical activity of the brain, impedance, neurotransmitter levels, levels of neurotransmitter breakdown products, medication levels, hormone levels, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for renal artery stenosis (i.e., narrowing or blockage of the artery that supplies the kidney) is carried out according to the following sequence of procedures:

1. An SCU 160 is implanted so that its electrodes 172 are positioned near renal artery 124 and its infusion outlet (s) 182 are located in or near one or both renal ganglion 122 and aorticorenal ganglion 120. If necessary or desired, electrodes 172' and/or outlets 182' may additionally or alternatively be located in or near the smooth muscle of the renal artery and/or arteriole(s).
2. Using Function 2 described above (i.e., transmitting data) of external electronic appliance 230 and external appliance 220, SCU 160 is commanded to produce a series of electrical stimulation pulses, possibly with gradually increasing amplitude, and possibly while infusing gradually increasing amounts of a sympathetic excitatory neurotransmitter antagonists, e.g., an antiadrenergic medication, such as phentolamine, or a prostaglandin, such as $PGE_2$.
3. After each electrical/infusion stimulation pulse, or at some other predefined interval, any change in renal artery or arteriole blood pressure resulting from the electrical and/or drug stimulation is sensed, preferably by one or more electrodes 172, 172' . These responses are converted to data and telemetered out to external electronic appliance 230 Function 3.
4. From the response data received at external appliance 230 from SCU 160, the stimulus threshold for obtaining a response is determined and is used by a clinician 242 acting directly 238 or by other computing means 248 to transmit the desired electrical and/or drug stimulation parameters to SCU 160 in accordance with Function 2.
5. When patient 208 desires to invoke electrical stimulation and/or drug infusion, patient 208 employs controller 210 to set SCU 160 in a state where it delivers a prescribed stimulation pattern, preferably from a predetermined range of allowable stimulation patterns.
6. To cease electrical and/or drug stimulation, patient 208 employs controller 210 to turn off SCU 160.
7. Periodically, the patient or caregiver recharges the power source/storage device 166 of SCU 160, if necessary, in accordance with Function 1 described above (i.e., transmit electrical power).

For the treatment of any of the various medical conditions responsive to modulation of circulatory perfusion, it may be desirable to modify or adjust the algorithmic functions performed by the implanted and/or external components, as well as the surgical approaches, in ways that would be obvious to skilled practitioners of these arts. For example, it may be desirable to employ more than one SCU 160, each of which could be separately controlled by means of a digital address. Multiple channels and/or multiple patterns of electrical and/or drug stimulation might thereby be programmed by the clinician and controlled by the patient in order to deal with complex or multiple symptoms or conditions such as may occur as a result of peripheral vascular disease.

In one preferred embodiment discussed earlier, SCU 160, or a group of two or more SCUs, is controlled via closed-loop operation. A need for and/or response to stimulation is sensed via SCU 160, or by an additional SCU (which may or may not be medicated to the sensing function), or by another implanted or external device. In some cases, the sensing and stimulating are performed by one SCU. If necessary, the sensed information is transmitted to SCU 160. Preferably, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

An example of the preferred closed-loop operation involves modulating circulatory perfusion in coordination with the delivery of one or more medications. An SCU modulates perfusion with electrical and/or drug stimulation, as described earlier, and preferably coordinates with medication infusion via the same SCU, or an additional SCU. Instead of delivering the medication(s) via an SCU, the drug(s) may be delivered via an external delivery device. The perfusion modulating SCU, which may also be delivering the medication(s), preferably synchronizes and controls the timing and duration of medication delivery. The medication delivery device (which may be part of the same SCU, a different SCU, or an external delivery device) preferably provides a feedback signal that lets the perfusion modulating SCU know it has received and understood the command(s). Alternatively, the medication infusion device may synchronize and control the timing and duration of the electrical and/or drug stimulation, while the perfusion modulating SCU preferably provides feedback that it has received and understood the command(s). These communication signal(s) are preferably encoded to prevent inadvertent delivery of stimulation or medication by other signals.

Figure 7:
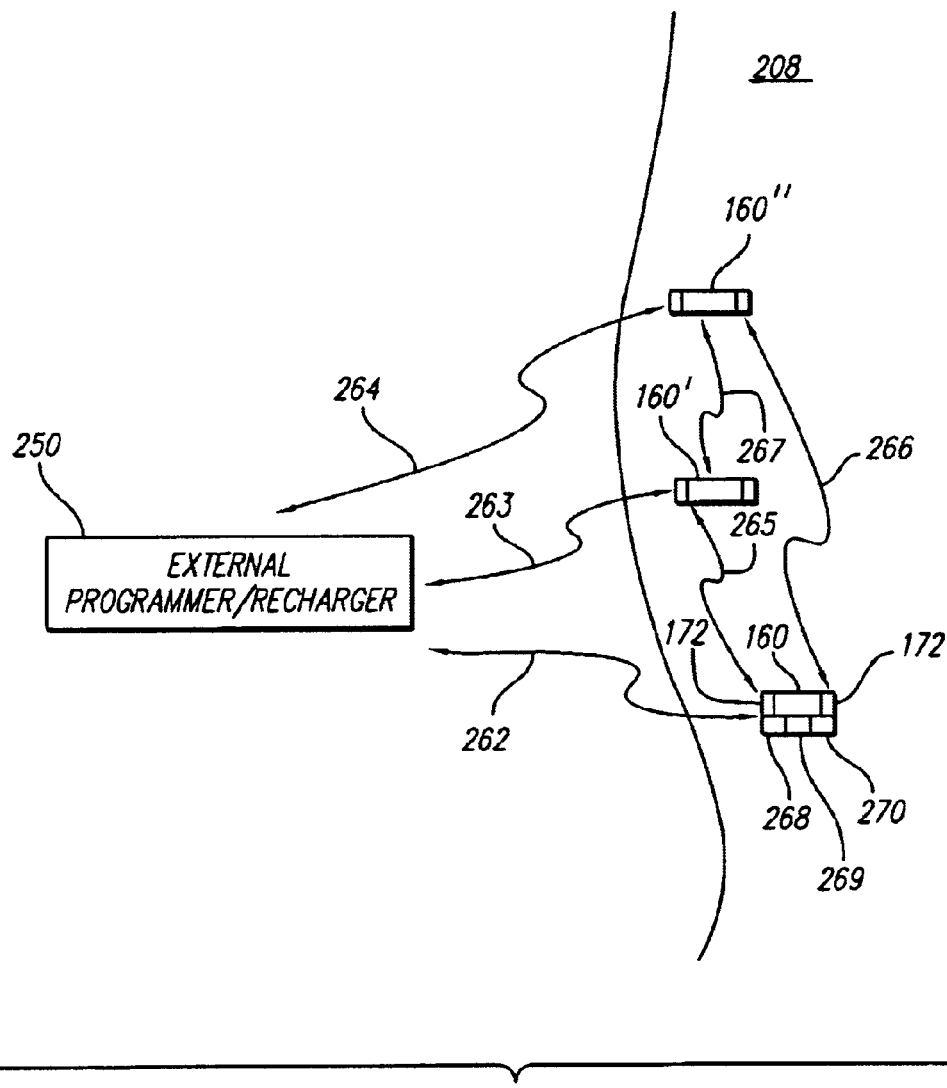
FIG. 7 depicts a system of implantable devices that communicate with each other and/or with external control/programming devices.

For instance, as seen in FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body as shown by the control lines 262, 263 and 264 in FIG. 7. That is, in accordance with one embodiment of the invention, the external controller 250 controls the operating of each of the implanted devices 160, 160' and 160". According to another embodiment of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, or an optical link. Specifically, as illustrated in FIG 7, SCU 160, 160', and/or 160", made in accordance with the invention, may communicate with an external remote control (e.g., patient and/or physician programmer 250) that is capable of sending commands and/or data to implanted devices and that is capable of receiving commands and/or data from implanted devices.

A drug infusion stimulator made in accordance with the invention preferably incorporates communication means for communicating with one or more external or site-specific drug delivery devices, and further has the control flexibility to synchronize and control the duration of drug delivery. The associated drug delivery device typically provides a feedback signal that lets the control device know it has received and understood commands. Again, the communication signal between the implanted stimulator and the drug delivery device is encoded to prevent the accidental on inadvertent delivery of drugs by other signals.

An SCU made in accordance with the invention further incorporates, in one embodiment, first sensing means 268 for sensing therapeutic effects, clinical variables, or other indicators of the state of the patient, such as blood pressure, blood flow, oxygen saturation, acidity/alkalinity, EMG, ENG, or EEG. The stimulator additionally or alternatively incorporates second means 269 for sensing neurotransmitter levels and/or their associated breakdown product levels, medication levels and/or other drug levels, hormone, enzyme, and/or cytokine levels and/or changes in these or other substances in the blood plasma. The stimulator additionally or alternatively incorporates third means 270 for sensing electrical current levels and waveforms supplied by another source of electrical energy. Sensed information may then be used to control the infusion and/or electrical parameters of the stimulator(s) in a closed loop manner, as shown by control lines 265, 266, and 267. Thus, the sensing means may be incorporated into a device that also includes electrical and/or drug sensing means (that may or may not have stimulating means), may communicate the sensed information to another device(s) with stimulating means.

As described earlier, there are numerous therapeutic uses of circulatory perfusion modulation, and many have been previously described herein. Additional uses will become apparent to those of skill in the art upon review of this document. As such, the previous and following examples should not be considered an exhaustive list, but rather illustrative of these uses.

A patient with a malignant tumor, such as in malignant breast cancer, is preferably treated with infusion of a chemotherapy medication, such as 5-fluorouracil (5-FU), doxorubicin (Adriamycin), and/or cyclophosphamide (FAC). The drug(s) are preferably delivered locally, with an SCU or transcutaneously, or may be delivered systemically with an external delivery device. An SCU (which may also be delivering the medication) preferably delivers electrical and/or drug stimulation to modulate the perfusion of tissue surrounding the tumor. For instance, if the tumor is located in the breast, and the medication is delivered locally, it is preferable to cause hypoperfusion of the smooth muscle of the arterioles of the breast. This advantageously focuses the medication in the localized tissues. If instead the medication is delivered systemically, it is preferable to cause hyperperfusion of the smooth muscle of the breast. This preferentially delivers the medication(s) to the area(s) of increased perfusion.

In this case, to modulate the perfusion of the smooth muscle of the breast, electrical stimulation may be applied via SCU as previously described, directly to the smooth muscle, or to the autonomic nerves, nerve ganglia, and/or other sites of autonomic synapses affecting innervation of the breast. Additionally or alternatively, stimulating drugs may be delivered via the same or an additional SCU to the autonomic ganglia or other sites of autonomic synapses, directly to the smooth muscle, and/or to vascular tissue supplying the breast.

In another example, a patient with cardiac ischemia will likely find relief from dilation of the coronary arteries. Therefore, electrical and/or drug stimulation may be applied to autonomic sites responsible for innervation of the coronary arteries (e.g., the sympathetic nerves arising from the cervical sympathetic trunk), and/or may be applied directly to the smooth muscle surrounding these arteries. As described above, either high frequency electrical stimulation or low frequency currents of 1–10 m. A applied for 1–30 minutes applied directly to the smooth muscle will likely lead to relaxation of smooth muscle. Electrical stimulation applied to the autonomic fibers may also cause the arteries to dilate. For example, high frequency electrical stimulation applied to sympathetic targets and/or low frequency electrical stimulation applied to parasympathetic targets are possible therapies in this case.

Additionally or alternatively, a stimulating drug(s) such as a sympathetic excitatory neurotransmitter antagonist (e.g. an adrenergic receptor antagonist, such as phentolamine) or an inhibitory neurotransmitter agonist (e.g. a GABA agonist, such as diazepam) may be infused at a sympathetic synapse affecting the coronary arteries, or may be applied directly to the smooth muscle. A parasympathetic excitatory neurotransmitter agonist (e.g. a cholinergic receptor agonist, such as bethanechol) or an inhibitory neurotransmitter antagonist may be infused at or near a parasympathetic synapse, or may be applied to the smooth muscle.

A patient suffering from peripheral vascular disease will likely find relief with techniques described above for dilating coronary arteries. In addition, modulating the contractile state of skeletal muscles may provide useful for these patients, due to the increased circulatory perfusion in the surrounding area. Low frequency stimulation applied to the skeletal muscle causes contraction of the muscle, while high frequency stimulation may cause the muscle to relax. Modulating the electrical frequency therefore modulates the contractile state of the muscle, which in turn modulates circulatory perfusion in the area.

In yet another alternative, sensing means described earlier may be used to orchestrate first the activation of SCU(s) targeting one or more nerves or muscles to modulate circulatory perfusion in one area, and then, when appropriate, the SCU(s) targeting nerves or muscles that modulate perfusion in another area and/or by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for modulating circulatory perfusion in coordination with delivery of medication, comprising:

implanting at least one system control unit in the body of the patent, wherein the at least one unit controls the delivery of at least one electrical stimulus to at least a first predetermined area affecting circulatory perfusion;

applying the at least one stimulus to the at least first predetermined area in order to modulate circulatory perfusion in at least a second area of the patient being treated wherein the at least second area includes tissue targeted to receive medication;

delivering medication to the at least second area of the patient being treated; and modifying the stimulus applied to the at least first predetermined area to cause hyperfusion in the at least second area, wherein perfusion of the medication is restricted due to the hyperfusion in the second area of the patient being treated.

2. The method of claim 1 wherein the first area and the second area are the same area.

3. The method of claim 1 wherein the electrical stimulus is delivered to at least one of a smooth muscle and a skeletal muscle at greater than about 50 to 100 Hz to relax the at least one smooth muscle and skeletal muscle.

4. The method of claim 1 wherein the electrical stimulus is delivered to at least one of a smooth muscle and a skeletal muscle at less than about 50 to 100 Hz to excite the at least one smooth muscle and skeletal muscle.

5. The method of claim 1 wherein the electrical stimulus is delivered to at least one smooth muscle at less than about 1–10 mA to relax the at least one smooth muscle.

6. The method of claim 1 wherein the medication is delivered locally.

7. The method of claim 1 further comprising implanting more than one system control unit.

8. The method of claim 1 further comprising sensing a condition and using the sensed condition to automatically determine the stimulus to apply.

9. A method for modulating circulatory perfusion in coordination with delivery of medication, comprising:

implanting at least one system control unit in the body of the patient, wherein the at least one unit controls the delivery of electrical stimulation to at least a first predetermined area affecting circulatory perfusion;

applying the electrical stimulation to the at least first predetermined area in order to modulate circulatory perfusion in at least a second area of the patient being treated wherein the at least second area includes tissue targeted to receive medication;

delivering medication to the at least third area of the patient being treated; and modifying the stimulus applied to the at least first predetermined area to cause hyperperfusion in the at least second area, wherein the medication is focused into the second area of the patient due to the hyperperfusion in the second area of the patient being treated.

10. The method of claim 9 wherein the medication is delivered to the bloodstream from at least one of an artery and a vein.

11. The method of claim 9 wherein the medication is delivered systemically.

12. The method of claim 9 further comprising implanting more than one system control unit.

13. The method of claim 9 wherein the first area and the second area are the same area.

14. The method of claim 9 wherein the electrical stimulation excites parasympathetic neural activity.

15. The method of claim 9 wherein the electrical stimulation inhibits sympathetic neural activity.

16. The method of claim 9 wherein the electrical stimulation is delivered at less than about 1–10 mA.

17. The method of claim 9 further comprising sensing a condition and using the sensed condition to automatically determine the stimulus to apply.

18. The method of claim 9 wherein the electrical stimulation is delivered to at least one of a smooth muscle and a skeletal muscle at greater than about 50 to 100 Hz to relax the at least one smooth muscle and skeletal muscle.

19. The method of claim 9 wherein the electrical stimulation is delivered to at least one of a smooth muscle and a skeletal muscle at less than about 50 to 100 Hz to excite the at least one smooth muscle and skeletal muscle.

* * * * *